US005698546A

United States Patent [19]
Bridger et al.

[11] Patent Number: 5,698,546
[45] Date of Patent: Dec. 16, 1997

[54] CYCLIC POLYAMINES

[75] Inventors: Gary J. Bridger, Bryn Mawr; Sreenivasan Padmanabhan, Exton; Renato T. Skerlj, Bryn Mawr, all of Pa.

[73] Assignee: Johnson Matthey Public Limted Company, London, England

[21] Appl. No.: 669,279

[22] PCT Filed: Jan. 6, 1995

[86] PCT No.: PCT/GB95/00019

§ 371 Date: Jun. 20, 1996

§ 102(e) Date: Jun. 20, 1996

[87] PCT Pub. No.: WO95/18808

PCT Pub. Date: Jul. 13, 1995

[30] Foreign Application Priority Data

Jan. 11, 1994 [GB] United Kingdom .................. 9400411

[51] Int. Cl.⁶ .................. C07D 487/02; A61K 31/395
[52] U.S. Cl. .................. 514/183; 540/471; 540/473
[58] Field of Search .................. 540/471, 473; 514/183

[56] References Cited

U.S. PATENT DOCUMENTS 5,021,409 6/1991 Murrer et al. .................. 514/183

FOREIGN PATENT DOCUMENTS 434385  6/1991  European Pat. Off. .
93-12096  6/1993  WIPO .

OTHER PUBLICATIONS

De Clercq et al: "Highly potent and selective inhibition of human immunodeficiency virus by the bicyclam derivative JM3100", Antimicrobial Agents and Chemotherapy, vol. 38, No. 4, 1994, pp. 668–674, see table I.

Mochizuki et al, Bull. Chem. Soc. Jpn. (1990), 63 (6), 1587–91.

Primary Examiner—Mukund J. Shah
Assistant Examiner—Bruck Kifle
Attorney, Agent, or Firm—Cushman Darby & Cushman IP Group Pillsbury Madison & Sutro LLP

[57] ABSTRACT

Linked polyamine cyclic compounds of general formula V—R—A—R'—W where V and W are independently cyclic polyamine moieties having from 9 to 32 ring members and 3 to 8 amine nitrogens and having either one or more aromatic rings fused thereto or a heteroatom other than nitrogen incorporated in the ring, A is an aliphatic or aromatic moiety and R and R' are each a linking chain, possess improved partition coefficients at biologically relevant pH compared to known compounds, and possess high anti-HIV activity.

17 Claims, 6 Drawing Sheets

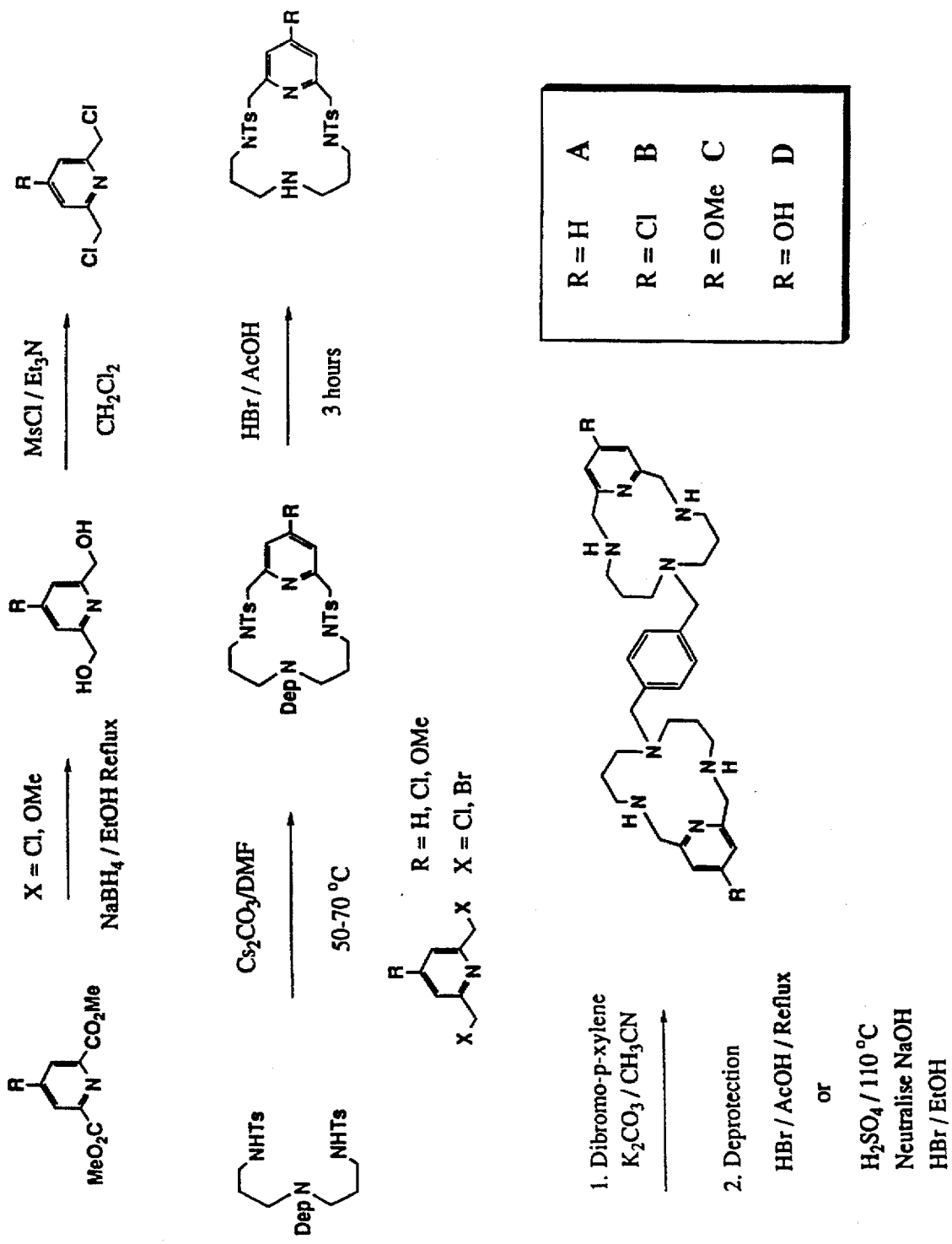

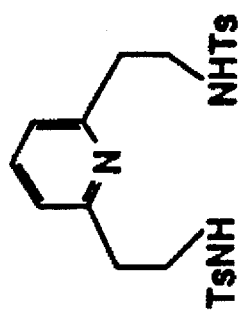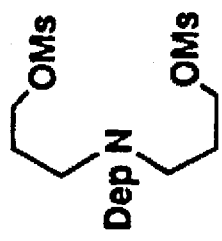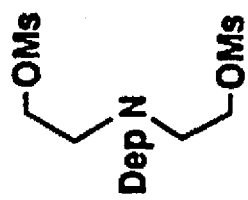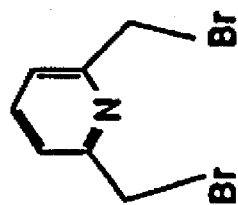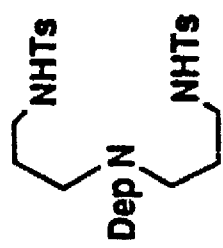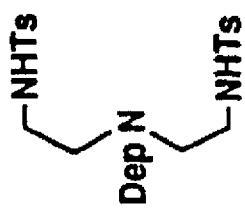

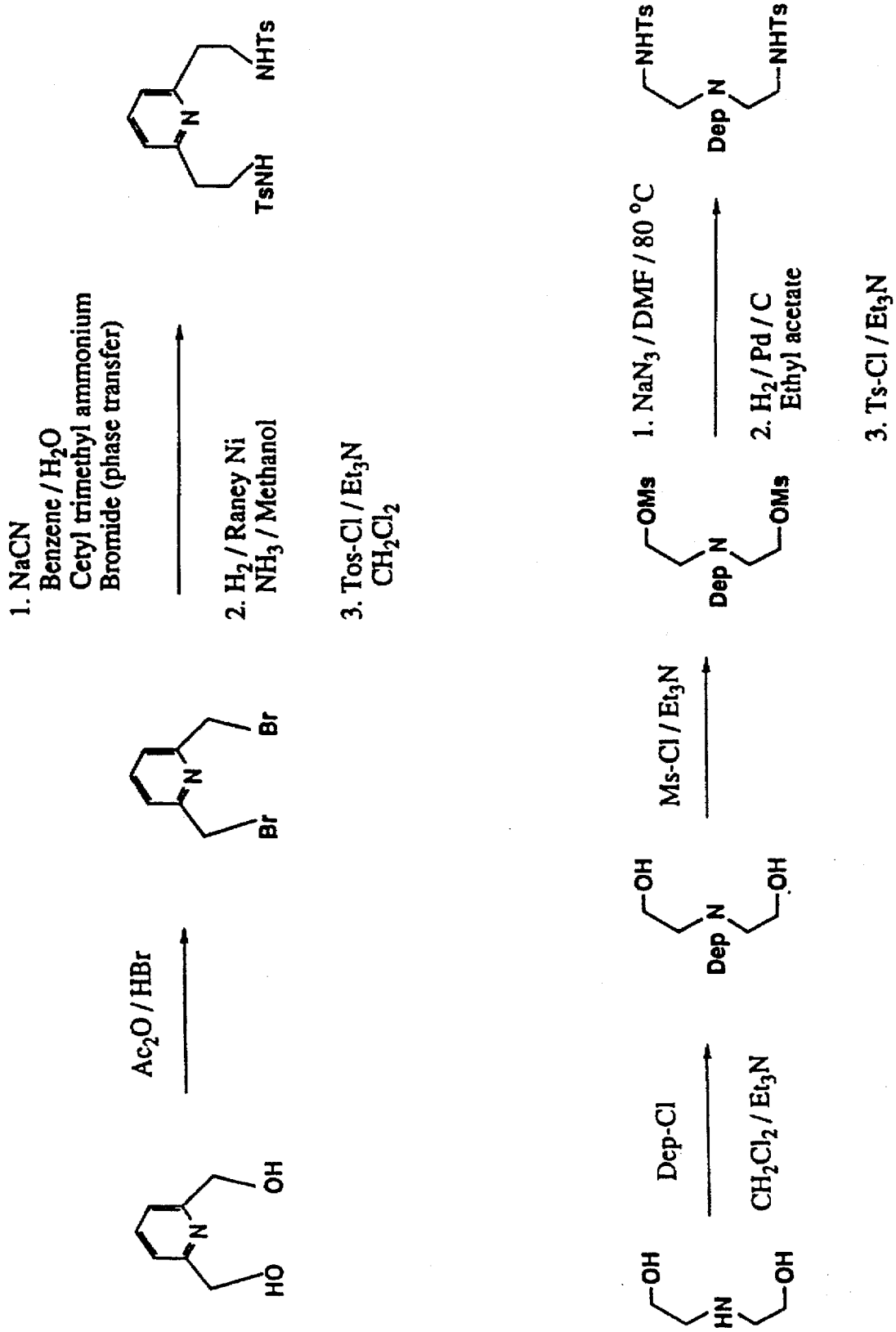

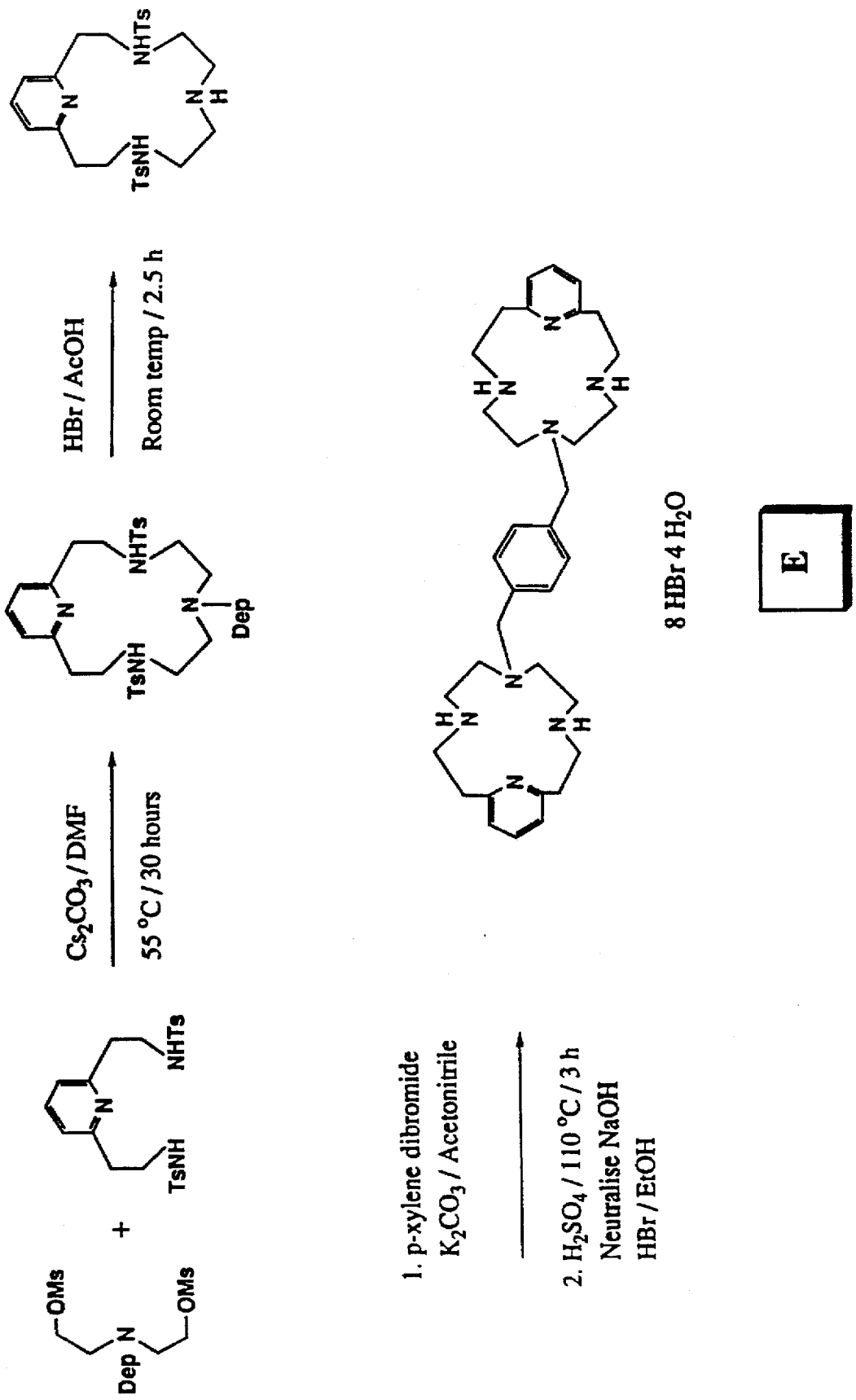

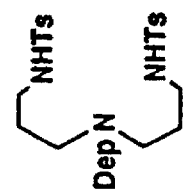
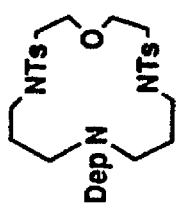
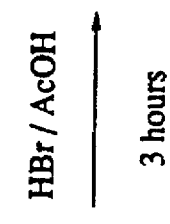
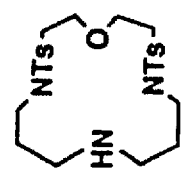
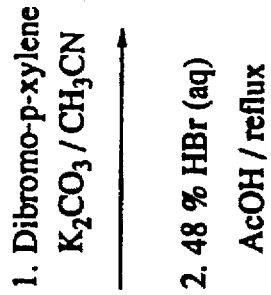
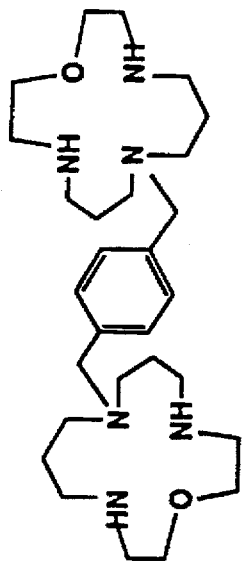
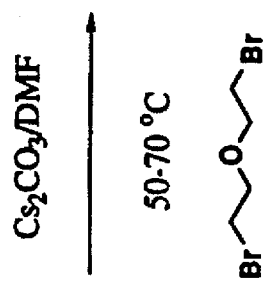
J

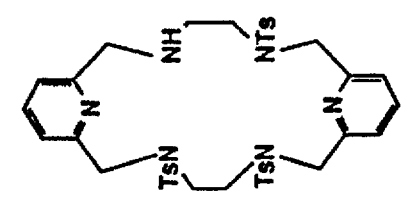
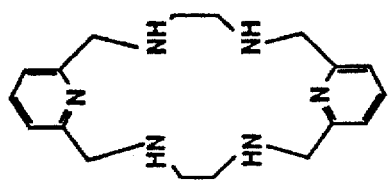
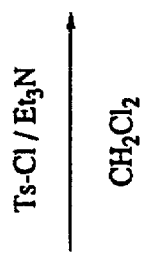
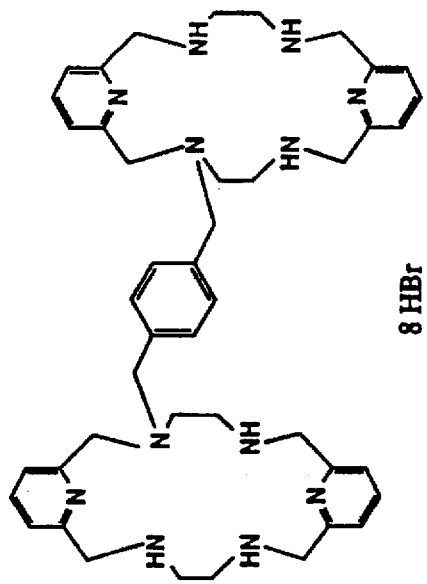
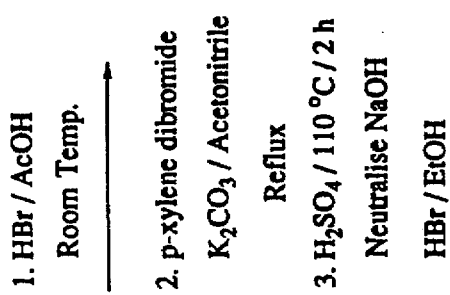

CYCLIC POLYAMINES

This application claims benefit of international application PCT/GB95/00019, filed Jan. 6,1995.

This invention concerns improvements in chemical compounds, more especially it concerns compounds and pharmaceutical compositions. In particular it concerns compositions and compounds having activity in in vitro tests on Human Immunodeficiency Virus-infected cells.

The disease known as Acquired Immune Deficiency Syndrome (AIDS) caused by infection by HIV has attracted immense research effort because of the effects of the disease on infected individuals and the dangers of the disease spreading to a wider section of the population. In general, although various chemotherapeutic treatments have been advocated, and some compounds have emerged as a potential basis for treatment, them is still a need for effective alternatives. In particular, most treatments such as the compound known as AZT have a high toxicity to cells and it would be desirable to find compounds which are less toxic. In man, the development of resistance to AZT has been identified as an additional clinical problem.

We have found a group of compounds which show protective properties in in vitro screens of cells challenged with HIV-1 and/or HIV-2, and are therefore indicated as useful for the treatment of AIDS and AIDS Related Complex and other viral and especially retroviral infections. Accordingly, the present invention provides the use of compounds defined below, in pharmaceutical compositions for treating HIV-infected patients. The invention further provides pharmaceutical compositions comprising a said compound in combination or association with a pharmaceutically acceptable diluent or excipient, for the treatment of HIV-infected patients. The invention may also be defined as the use of a said compound for the manufacture of a medicament for the treatment of HIV-infected patients. The invention further provides a process for the production of a pharmaceutical composition for the treatment of an HIV-infected patient, comprising the combination of a compound as defined below with a pharmaceutically acceptable diluent or excipient, and formulating said composition into a form suitable for administration to said patient. The invention also provides a method of treatment of an HIV-infected patient, comprising administering to said patient an effective dose of a said compound. It is understood that treatment includes prophylactic treatment of patients at risk, in view of the protective properties observed. The use of the compounds may also be stated as a method of treating HIV-infected or HIV-challenged human cells to prevent or modulate the multiplication of the HIV, comprising administering to said cells an effective dose of a said compound.

A 2,2'-dimer of cyclam has been reported as being isolated as a 2% by-product in the synthesis of cyclam (1,4,8,11,tetraazacyclotetradecane) (Barefield et al, J C S Chem Comm (1981), 302). This compound was stated to be insoluble in water. We believe that the insoluble 2,2'-bicyclam is a mixture of the 2R, 2'R and 2S,2'S enantiomers; we have characterised a soluble dimer which we believe to be the meso 2R,2'S isomer. The 6,6'-bicyclam isomer has been reported by Fabbrizzi et al, Inorg Chem 25, 2671 (1986). Certain N,N'-linked bicyclic compounds have been reported by Ciampolini et al, Inorg Chem 26, 3527 (1987). No biological activity has been suggested for such compounds.

U.S. Pat. No. 4,156,683 discloses monocyclic and bicyclic macrocyclic compounds, which are said to have biological activity in regulating sodium, potassium and calcium levels in mammals. Additionally, a specific group of N-alkylated monocyclic compounds are said to possess activity against $A_2$ influenza viruses in a modified Hermann test on chick fibroblast tissue. It is also said that the preferred compounds, which form complexes of greater stability, are those having three bridging chains between bridgehead nitrogen atoms, that is fused bicyclic compounds.

Our U.S. Pat. No. 5,021,409 and WO 93/12096 describes linked cyclic compounds as being active against HIV-1 and HIV-2 in in vitro tests. We have now discovered that certain linked cyclic compounds exhibit interesting physical chemical properties indicating/hat they possess potential oral activity against HIV.

The present invention provides as active compounds linked cyclic compounds of the general formula I.

in which V and W are independently cyclic polyamine moieties having from 9 to 32 ring members and from3 to 8 amine nitrogens in the ring spaced by 2 or more carbon atoms from each other, and having one or more aromatic heteroaromatic rings fused thereto and/or a heteroatom other than nitrogen incorporated in the ring, A is a saturated or unsaturated straight or branched chain, aromatic or heteroaromatic moiety, and R and R' are each a substituted or unsubstituted alkylene chain or heteroatom-containing chain which spaces the cyclic polyamine and the moiety A. The invention also encompasses acid addition salts and metal complexes of the compounds of formula I.

In the above formula, the cyclic polyamine moieties V and W have the general formula II,

which may be substituted or unsubstituted at carbon or nitrogen non-linking atoms, suitably by hydroxyl, alkoxy, thiol, thioalkyl and any other groups which do not adversely effect the activity or toxicity of the compounds but may reduce the basicity of the amines eg halogen, nitro, carboxyl, carboxamido, sulphonic acid, phosphate.

The groups X and Y may be methylene or groups which impart lower basicity and suitable moieties are substituted carbon (with electron withdrawing groups), oxygen (eg hydroxylamine), carboxy (eg amide), carboximido (eg hydrazide) and nitrogen (eg hydrazine). The group Z may be a heteroatom and suitable atoms are nitrogen, oxygen, sulphur or an aromatic, fused aromatic, heteroaromatic or fused heteroaromatic group or joined aromatic such as biphenyl or bipyridyl and may be 5 or 6 membered. The aromatic groups may be linked into the macrocycle via ortho, meta or para substitution and either directly joined to X and Y or joined through saturated, unsaturated or polyunsaturated carbon atoms, preferably alkyl of 1–6 carbons, especially 1–3 carbon atoms. The heteroaromatic groups may be pyridine, pyrimidine, pyrazine, thiazole, imidazole, oxadole. Both the aromatic and heteroaromatic groups may be substituted at multiple non-linking positions with electron donating groups eg alkyl, thio, thioalkyl, hydroxyl, alkoxy, amine and derivatives thereof, or electron withdrawing groups or atoms eg nitro, halogen, carboxyl, carboxamido, sulphonic acid and derivatives that do not substantially adversely effect toxicity or activity.

V and W may be identical or non-identical, although it is convenient that they are identical.

The aromatic or heteroaromatic moiety A in general formula I, tethers V and W through the linking groups R and R'. Moiety A may be phenyl or fused aromatic such as napthyl, heterocyclic such as pyridyl or thiophenyl, fused heterocyclic or joined aromatic, or joined heteroaromatic, for example biphenyl or bipyridyl respectively. The moiety A may also be substituted at single or multiple non-linking positions with electron-donating groups, eg alkyl, thio, thioalkyl, hydroxyl, alkoxyl, amine and derivatives thereof, or electron-withdrawing groups or atoms, eg nitro, halogen, carboxy, carboxamido, sulphonic acid and derivatives thereof.

The moiety A may also be aliphatic, branched aliphatic, unsaturated or polyunsaturated and contain heteroatoms such as nitrogen, oxygen, sulphur. Preferred chain lengths are of 1–10 atoms, especially 1–6 carbons.

The linking group R may contain heteroatoms, eg O, N or S, and may be saturated, unsaturated or polyunsaturated, and is preferably alkyl or cycloalkyl of 1 to 12 atoms, more preferably alkyl of 1 to 6 carbon atoms, especially alkyl of 1 to 3 atoms.

The invention also includes what may be termed "pro-drugs", that is protected forms of the linked cyclic compounds, which release the compound after administration to a patient. For example, the compound may carry a protective group which is split off by hydrolysis in body fluids, eg in the bloodstream, thus releasing active compound or are oxidised or reduced in body fluids to release the compound, for example pyridine N-oxides. A discussion of pro-drugs may be found in "Smith and Williams' Introduction to the Principles of Drug Design", H. J. Smith, Wright, 2nd Edition, London 1988.

The invention further provides a method for the production of the compounds of formula I, which method comprises nucleophilic attack by cyclic polyamines V' and W' each having a single unprotected ring amine nitrogen, all other ring amine nitrogens being protected, on a compound of formula III

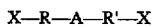

X—R—A—R'—X        (III)

wherein R, R' and A are as defined above, and each X is an active substituent which can be displaced by the unprotected nitrogens of polyamines V' and W' and is preferably selected from Br, Cl, I, methanesulphonate, 4-tolylsulphonate and trifluoromethane sulphonate, and subsequently de-protecting the ring amine nitrogens.

It is well within the capabilities and knowledge of the skilled synthetic chemist to protect the amine nitrogens of cyclic polyamines, and it is preferred to use substitution by methanesulphonyl and/or 4-tolsulphonyl and/or diethylphosphoryl. The compounds of formula III are known or may be synthesised by generally known techniques.

The reaction is preferably carried out in a solvent, such as acetonitrile or dimethylformamide, tetrahydrofuran or dioxane and in the presence of a base, for example sodium carbonate or potassium carbonate. The reaction generally takes place readily at room temperature to elevated temperature, to give a linked molecule having protected amine nitrogen atoms. In general, a mixture of products will be obtained, and we have found that chromatography on silica gel is a particularly convenient method of separation.

The de-protection step is suitably carried out by refluxing the protected molecule in a mixture of aqueous HBr and acetic acid or concentrated sulphuric acid or in the case of diethylphosphoryl in the presence of hydrogen chloride (gas) in acetic acid.

It is convenient that V and W are identical, so that the compound of formula II is reacted with two equivalents of the protected polyamine.

In the case where V and W are not identical and moiety A is aromatic as defined above, it is appropriate to modify the process described above using as reactant a compound of formula IIIa.

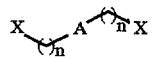

X is a halogen, preferably chlorine, bromine, iodine, tosyl or mesyl and each n, n' is a positive integer such as to yield chain R, R' in the product.

The protected polyamine V' is firstly reacted with a 5–10 fold excess of a compound of formula IIIa, then secondly reacting this product with a protected polyamine W'. Both stages are carried out using conditions described above, preferably using a solvent such as acetonitrile in the presence of a base such as sodium carbonate or potassium carbonate. Following chromatographic purification, the ring amine nitrogens are de-protected as described above.

In the case where V and W are not identical and moiety A is aliphatic as defined above, it is appropriate to modify the process described above, using as reactant a compound of formula IIIb.

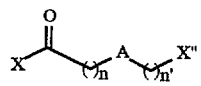

in which A is as defined above,

X' is a halogen, preferably bromine or chlorine

X" is a halogen, preferably bromine or iodine, or tosyl or mesyl, and n=0 or a positive integer such as to yield chain R in the product, and n'=a positive integer such as to yield chain R' in the product, and reacting firstly with a protected cyclic polyamine V' and secondly reacting the reaction product with a protected cyclic polyamine W', subsequently reducing the carbonyl group on the chain, and thereafter de-protecting the ring amine nitrogens.

The first stage reaction is conveniently carried out in a solvent, for example dichloromethane or chloroform with triethylamine, and the second stage reaction is conveniently carried out under the conditions described above, that is in a solvent and in the presence of a base. Before de-protection, which may be accomplished as described above, it is necessary to reduce the carbonyl group on the linking chain using a reducing agent such as borane or lithium aluminium hydride, in manner generally known. The skilled synthetic chemist will be able to carry into effect the process of the invention in its various stages and possible variants.

The compounds are indicated for the treatment of vital infections, especially retrovirus infections and particularly HIV infections, and the compounds of formula I are to be considered as active compounds for the pharmaceutical compositions, processes for making the same and methods of treatment mentioned above. In these aspects of the invention, it is to be understood that meso forms, enantiomers and resolved optically active forms of the compounds of formula I are included. Also, it is to be considered within the invention, compounds of formula I diluted with non-toxic or other active substances.

Acid addition salts, for example hydrochlorides, and non-toxic labile metal complexes of the compounds of formula I are also active compounds according to the present invention. Non-toxic in the present context has to be considered with reference to the prognosis for the infected patient without treatment. Copper and zinc complexes are preferred although other metals such as nickel may be considered, whereas less labile metal atoms such as cobalt and rhodium are less preferred because of likely lower selectivity.

The present invention will now be illustrated by the following preparative Examples.

EXAMPLE 1 a) N-Diethoxyphosphoryl-3,3'-iminodipropionitrile

To a solution of 3,3'-iminodipropionitrile (2.0 g, 16 mmol) and triethylamine (2.7 ml) in dichloromethane (50 ml) was added dropwise with stirring, under Argon, a solution of diethylchlorophosphate (2.8 g, 16 mmol) in dichloromethane (20 ml) over approximately 30 minutes and then allowed to stir overnight at room temperature. The mixture was washed with brine (50 ml) then dried ($Na_2SO_4$) and evaporated in vacuo giving N-diethoxyphosphoryl-3,3'-iminodipropionitrile (2.7 g, 64%) as a colourless oil.

b) N-Diethoxyphosphoryl-3,3'-iminobispropylamine

To a solution of N-diethoxyphosphoryl-3,3'-iminodipropionitrile (1.0 g, 4 mmol) in methanol (50 ml, saturated with ammonia) was added Raney nickel: (5.0 g, excess) and the mixture was hydrogenated at 45 psi and room temperature for 48. hours. The catalyst was filtered off and the solvent evaporated in vacuo to give N-diethoxyphosphoryl-3,3'-iminobispropyl amine (0.95 g, 92%) as a colourless viscous oil.

c) N-Diethoxyphosphoryl-N',N"-bis(p-toluenesulphonyl)-3,3'-iminobispropylamine To a solution of N-diethoxyphosphoryl-3,3'-iminobispropylamine (1.0 g, 4 mmol) and triethylamine (1.2 ml) in dichloromethane (50 ml) was added dropwise with stirring a solution of p-toluenesulphonyl chloride (1.6 g, 7 mmol, 2.2 equiv.) in dichloromethane (25 ml) over approximately 15 minutes and then allowed to stir at room temperature overnight. The mixture was washed with dilute hydrochloric acid (50 ml), saturated aqueous sodium bicarbonate (50 ml) and brine (50 ml) then dried ($Na_2SO_4$) and evaporated in vacuo to give the crude product as a brown oil. The crude product was purified by column chromatography on silica gel using dichloromethane/methanol (97/3) as eluent, giving N-diethoxyphosphoryl-N',N"-bis(p-toluenesulphonyl)-3,3'-imminodipropyl amine (0.9 g, 43%) as a white solid.

d) 7-Diethoxyphosphoryi-3,11-bis(p-toluenesulphonyl)-3,7,11,17-tetraaza-bicyclo[13.3.1]heptadeca-1(17),13,15-triene General Procedure:

To a solution of N-diethoxyphosphoryl-N',N"-bis(p-toluene-sulphonyl)-3,3'-iminobispropylamine (2.9 g, 5 mmol) in DMF (150 ml) containing finely ground anhydrous cesium carbonate (4.1 g, 13 mmol, 2.5 equiv.) stirred at 55°–60° C. under argon was added a solution of 2,6-bis-(dibromomethyl)pyridine hydrobromide [M E Haeg, B J Whitlock and H W Whirlock, *J Am Chem Soc*, 1989, 111, 692], (1.78 g, 5 mmol, 1.0 equiv.) in DMF (75 ml) dropwise over a period of 3–4 hours. After a total of 25–30 hours at 55°–60° C. the mixture was allowed to cool to room temperature and evaporated to dryness under reduced pressure. The residue was partitioned between dichloromethane (150 ml) and brine (150 ml). The organic layer was separated and the aqueous phase was extracted with two further portions of dichloromethane. The combined organic extracts were dried ($Na_2SO_4$) and evaporated in vacuo to give the crude product as a light brown solid. Column chromatography on silica gel using dichloromethane/methanol (98/2) as eluent, gave 7-diethoxyphosphoryl-3,11-bis(p-toluenesulphonyl)-3,7,11,17-tetraaza-bicyclo[13.3.1]-heptadeca-1(17),13,15-triene (2.1 g, 60%) as a white solid.

e) 3,11-Bis-(p-toluenesulphonyl)-3,7,11,17-tetraazabicyclo[13.3.1]-heptadeca-1(17),13,15-triene General Procedure:

To a solution of 7-diethoxyphosphoryl-3, 11-bis(p-toluenesulphonyl)-3,7,11,17-tetraazabicyclo[13.3.1]heptadeca-1(17),13,15-triene (500 mg) in glacial acetic acid (2.5 ml) was added 30% HBr/acetic acid (Aldrich, 1.5 ml) and the reaction mixture stirred at room temperature for 2½ hours. Ether (100 ml) was added to precipitate the product. The white solid was allowed to settle to the bottom of the flask and the supernatant solution was decanted off. The solid was then washed by decantation with ether three times and the remaining traces of ether removed by evaporation under reduced pressure. The solid was partitioned between sodium hydroxide solution (10 ml, 10N) and dichloromethane (150 ml) and the organic layer was separated, dried ($Na_2SO_4$) and evaporated in vacuo to give 3,11-bis(p-toluenesulphonyl)-3,7,11,17-tetraazabicyclo[13.3.1]heptadeca-1(17),13,15-triene (290 mg, 74%) as a white solid.

f) 7,7'-[1,4-Phenylenebis(methylene)]bis[3,11-bis(p-toluene-sulphonyl)-3,7,11,17-tetraazabicyclo[13.3.1]heptadeca-1(17),13,15-triene]

General Procedure

To a solution of 3,11-bis(p-toluenesulphonyl)-3,7,11,17-tetraazabicyclo[13.3.1]-heptadeca-1(17),13,15-triene (280 mg, 0.52 mmol) and potassium carbonate (108 mg, 0.77 mmol, 1.5 equiv.) in acetonitrile (30 ml) was added α,α'-dibromo-p-xylene (68 mg, 0.26 mmol, 0.5 equiv.) and the mixture heated to reflux overnight with rapid stirring. The reaction mixture was allowed to cool to room temperature then evaporated and the residue was partitioned between dichloromethane (100 ml) and brine (50 ml). The organic layer was separated and the aqueous layer was extracted with two further portions of dichloromethane. The combined organic extracts were dried ($Na_2SO_4$) and evaporated to dryness under reduced pressure and the residue was purified by column chromatography on silica gel using methanol/dichloromethane (98/2) as eluant to give 7,7'-[1,4-phenylene-bis(methylene)]bis[3,11-bis(p-toluenesulphonyl)-3,7,11,17-tetraazabicyclo[13.3.1]-heptadeca-1(17), 13,15-triene] (297 mg, 97%) as a white solid.

Synthesis of Compound A 7,7'-[1,4-Phenylenebis(methylene)]bis-3,7,11,17-tetraazabicyclo[13.3.1heptadeca-1(17),13,15-triene hexahydrobromide hexahydrate To a solution of 7,7'-[1,4-phenylenebis(methylene)]bis[3, 11-bis(p-toluenesulphonyl)-3,7,11,17-tetraazabicyclo

[13.3.1]heptadeca-1(17),13,15-triene (150 mg, 0.13 mmol) in acetic acid (2.5 ml) was added hydrobromic acid (Aldrich 48% aqueous, 1.5 ml) and the mixture was heated to reflux with stirring for 18 hours. The mixture was allowed to cool and ether (50 ml) was added to precipitate the product. The white solid was allowed to settle to the bottom of the flask and the supernatant solution was decanted off. The solid was then washed by decantation with ether three times and the remaining traces of ether removed by evaporation under reduced pressure giving 7,7'-[1,4-phenylenebis(methylene)]bis-3,7,11,17-tetraazabicyclo[13.3.1]heptadeca-1(17),13,15-triene hexahydrobromide hexahydrate (60 mg, 39%) as a white solid. $^1$H NMR (D$_2$O) δ 2.22 (m, 8H), 3.03 (m, 8H), 3.27 (m, 8H), 4.35 (s, 4H), 4.43 (s, 8H), 7.44 (d, 4H, J=7.5 Hz), 7.49 (s, 4H), 7.85 (t, 2H, J=7.5 Hz). Mass spectrum (FAB); m/e (relative intensity); 653 (M+HBr, 13), 651 (M+HBr, 13), 571 (M+1, 48), 339 (58), 235 (100). C$_{34}$H$_{68}$N$_8$Br$_6$O$_6$ requires: :C, 35.07; H, 5.89; N, 9.62; Br, 41.17; found: C, 35.54; H, 5.53; N, 9.37; Br, 40.04.

EXAMPLE 2

4-Chloro-2,6-bis(hydroxymethyl)pyridine

To a stirred solution of dimethyl 4-chloropyridine-2,6-dicarboxylate (5 g, 21.83 mmol) (D G Markees and G W Kidder, *J Am Chem Soc* 1956, 78, 4130) in 200 ml of anhydrous EtOH was added sodium borohydride (3.31 g, 87.33 mmol) and the mixture gently refluxed under an argon atmosphere for 16 hours. The solution was cooled to room temperature and concentrated to dryness. Ethyl acetate (50 ml) and H$_2$O (50 ml) was added to the residue and the aqueous phase was extracted with ethyl acetate (x3), dried over MgSO$_4$ and concentrated in vacuo thus affording a whim solid which was identified by $^1$H NMR as 4-chloro-2,6-bis(hydroxymethyl)pyridine (2.41 g, 64%).

4-Chloro-2,6-bis(chloromethyl)pyridine

To a stirred solution of 4-chloro-2,6-bis(hydroxymethyl)pyridine (2.41 g, 13.93 mmol) and triethylamine (7.8 ml, 55.72 mmol) at 0° C. in 100 ml of anhydrous dichloromethane and 50 ml of anhydrous chloroform under an argon atmosphere was added methanesulfonyl chloride (3.2 ml, 41.79 mmol). The solution was stirred at 0° C. for 30 minutes, warmed to room temperature and stirred a further 36 hours. The reaction mixture was quenched with water (50 ml), the aqueous phase extracted with dichloromethane, dried (MgSO$_4$) and concentrated in vacuo to afford a red-orange oil. The residual oil was passed through a short plug of silica gel using dichloromethane as eluent thus affording after concentration a pale yellow solid which was identified by $^1$H NMR as 4-chloro-2,6-bis-(chloromethyl)pyridine (1.9 g, 65%).

15-Chloro-7-diethoxyphosphoryl-3,11-bis(p-toluenesulphonyl)-3,7,11,17-tetraazabicyclo[13.3.1]heptadeca-1(17),13,15-triene Using the general procedure in example 1d:
N-Diethoxyphosphoryl-N',N"-bis(p-toluenesulphonyl)-3,3'-iminobis-propylamine (1.8 g, 3.13 mmol) and 4-chloro-2,6-bis(chloromethyl)pyridine (660 mg, 3.13 mmol) gave 15-chloro-7-diethoxyphosphoryl-3,11-bis(p-toluenesulphonyl)-3,7,11,17-tetraazabicyclo[13.3.1]-heptadeca-1(17),13,15-triene (640 mg, 29%) as a fluffy white solid.

15-Chloro-3,11-bis(p-toluenesulphonyl)-3,7,11,17-tetraazabicyclo-[13.3.1]heptadeca-1(17),13,15-triene Using the general procedure in example 1e 15-Chloro-7-diethoxyphosphoryl-3,11-bis(p-toluenesulphonyl)-3,7,11,17-tetraaza-bicyclo[13.3.1] heptadeca-1(17),13,15-triene (640 mg, 0.899 mmol) gave15-chloro-3,11-bis(p-toluenesulphonyl)-3,7,11,17-tetraazabicyclo[13.3.1]-heptadeca-1(17),13,15-triene (440 mg, 85%) as a white solid.

7,7'-[1,4-Phenylenebis(methylene)]bis[15-chloro-3,11-bis(p-toluenesulphonyl)-3,7,11,17-tetraazabicyclo [13.3.1]heptadeca-1(17),13,15-triene]

Using the general procedure in example 1f

15-Chloro-3,11-bis(p-toluenesulfonyl),3,7,11,17-tetraazabicyclo-[13.3.11heptadeca-1(17),13,15-triene (430 mg, 0.746 mmol) and α,α'-dibromo-p-xylene (99 mg, 0.373 mmol) gave 7,7'-[1,4-phenylenebis(methylene)]bis[15-chloro-3,11-bis-(p-toluenesulphonyl)-3,7,11,17 hexaazabicyclo[13.3.1]heptadeca-1(17),13,15-triene] (280 mg, 60%) as a white solid.

Synthesis of Compound B

7,7'-[1,4-Phenylenebis(methylene)]bis[15-chloro-3,7,11,17-tetraazabicyclo[13.3.1]heptadeca-1(17),13,15-triene]hexahydrobromide monoacetate A solution of 7,7'-[1,4-phenylenebis(methylene)]bis[15-chloro-3,11-bis(p-toluenesulphonyl)-3,7,11,17-hexaazabicyclo[13.3.1]heptadeca-1(17),13,15-triene] (270 mg, 0.215 mmol) in conc. H$_2$SO$_4$ (3 ml) was stirred at 110° C. for 2 hours. The dark brown solution was cooled to room temperature and the pH adjusted to 14 with 10N NaOH. The aqueous phase was extracted with CHCl$_3$ (20 ml, x 3), the combined organic phases were dried (MgSO$_4$) and concentrated in vacuo affording a pale yellow oil. To a stirred solution of the oil in 5 ml of anhydrous EtOH was passed HBr (g) resulting in a pale white precipitate. After stirring for 15 minutes at room temperature the solid was collected by filtration. The tan solid was dissolved in 5 ml of H$_2$O, activated charcoal was added (120 mg) and the solution was heated for 30 minutes. The hot solution was eluted through celite and concentrated to approximately 2 ml. Glacial acetic acid was added resulting in a white precipitate which was collected by filtration, washed with Et$_2$O and dried in vacuo giving 7,7'-[1,4-phenylenebis(methylene)]bis[15-chloro-3,11-bis(p-toluene-sulphonyl)-3,7,11,17,hexaazabicyclo [13.3.1]heptadeca1(17),13,15-triene]hexahydro-bromide monoacetate (90 mg, 35%) as a white solid. $^1$H NMR (D$_2$O) δ 2.10–2.24 (m, 8H), 3.00–3.12 (m, 8H), 3.12–3.24 (m, 8H), 4.21 (s, 4H), 4.40 (s, 8H), 7.39 (s, 4H), 7.53 (s, 4H). $^{13}$C NMR (D$_2$O): 19.46, 43.22, 48.33, 48.75, 58.38, 125.09, 130.6, 132.1, 147.1, 151.6. Mass spectrum (FAB); m/e (relative intensity); 721 (M+HBr, 51), 719 (M+HBr, 38), 639 (M+1, 100), 372 (18). C$_{36}$H$_{58}$N$_8$O$_2$Cl$_2$Br$_6$ requires C, 36.48; H, 4.93; N, 9.45; Cl, 23.93; Br, 53.94. Found: C, 36.05; H, 4.97; N, 9.54; Cl, 23.85; Br, 53.75.

EXAMPLE 3

4-Methoxy-2,6-bis(hydroxymethyl)pyridine

To a stirred solution of dimethyl 4-methoxypyridine-2,6-dicarboxylate (5 g, 20.8 mmol) (D G Markees and G W Kidder, *J Am Chem Soc* 1956, 78, 4130) in 200 ml of anhydrous EtOH was added sodium borohydride (3.17 g, 83.35 mmol) and the mixture gently refluxed for 16 hours under an argon atmosphere. The solution was cooled to room temperature and concentrated to dryness. Ethyl acetate (100 ml) and H$_2$O (50 ml) was added to the residue and the aqueous phase was extracted with ethyl acetate (x3), dried over MgSO$_4$ and concentrated in vacuo thus affording a white solid which was identified by $^1$H NMR as 4-methoxy-2,6-bis(hydroxymethyl)pyridine (2.89 g, 82%).

4-Methoxy-2,6-bis(chloromethyl)pyridine

To a stirred solution of 4-methoxy-2,6-bis(hydroxymethyl)pyridine (2.89 g, 17.10 mmol)-and triethylamine (9.6 ml, 68.40 mmol) at 0° C. in 100 ml of anhydrous dichloromethane and 50 ml of chloroform under an argon atmosphere was added methanesulphonyl chloride (3.9 ml, 51.30 mmol). The solution was stirred at 0° C. for 30 minutes, warmed to room temperature and stirred a further 24 hours. Additional methanesulphonyl chloride (1.5 ml, 19.38 mmol) was added and the mixture was stirred at 50° C. for 24 hours. The reaction mixture was quenched with H$_2$O (50 ml), the aqueous phase extracted with CH$_2$Cl$_2$, dried over MgSO$_4$ and concentrated to afford an orange oil. The residual oil was passed through a short plug of silica gel using dichloromethane as eluent thus affording after concentration a pale yellow solid which was identified by $^1$H NMR as 4-methoxy-2,6-bis-(chloromethyl)pyridine (2.3 g, 66%).

7-Diethoxyphosphoryl-15-methoxy-3,11-bis(p-toluenesulphonyl)-3,7,11,17-tetraazabicyclo[13.3.1]heptadeca-1(17),13,15-triene Using the general procedure in example 1d
N-Diethoxyphosphoryl-N',N"-bis(p-toluenesulphonyl)-3,3'-iminobis-propylamine (1.8 g, 3.13 mmol) and 4-methoxy-2,6-bis(chloromethyl)pyridine (650 mg, 3.13 mmol) gave 7-diethoxyphosphoryl-15-methoxy-3,11-bis(p-toluenesulphonyl)-3,7,11,17-tetraazabicyclo[13.3.1]heptadeca-1(17),13,15-triene (810 mg, 36%) as a fluffy white solid.

15-Methoxy-3,11-bis(p-toluenesulphonyl)-3,7,11,17-tetraazabicyclo-[13.3.1]-heptadeca-1(17),13,15-triene Using the general procedure in example 1e
7-Diethoxyphosphoryl- 15-methoxy-3,11-bis(p-toluenesulphonyl)-3,7,11,17-tetraazabicyclo[13.3.1]heptadeca-1(17),13,15-triene (800 mg, 1.13 mmol) gave 15-methoxy-3,11-bis(p-toluenesulphonyl)-3,7,11,17-tetraazabicyclo[13.3.1]-heptadeca-1(17),13,15-triene (615 mg, 95%) as a white solid.

7,7'-[1,4-Phenylenebis(methylene)]bis[15-methoxy-3,11-(p-toluenesulphonyl)-3,7,11,17-tetraazabicyclo[13.3.1]heptadeca-1(17),13,15-triene]

Using the general procedure in example 1f
15-Methoxy-3,11-bis(p-toluenesulphonyl)-3,7,11,17-tetraazabicyclo-[13.3.1]heptadeca-1(17),13,15-triene (610 mg, 1.066 mmol) and α,α'-dibromo-p-xylene (141 mg, 0.533 mmol) gave 7,7'-[1,4-phenylenebis(methylene)]bis[15-methoxy-3,11-(p-toluenesulphonyl)-3,7,11,17-tetraazabicyclo[13.3.1]heptadeca-1(17),13,15-triene](320 mg, 48%) as a white solid.

Synthesis of Compound C 7,7'-[1,4-Phenylenebis(methylene)]bis[15-methoxy-3,7,11,17-tetraazabicyclo-[13.3.1]heptadeca-1(17),13,15-triene] hexahydrobromide dihydrate A solution of 7,7'-[1,4-phenylenebis(methylene)]bis[15-methoxy-3,11-(p-toluenesulphonyl)-3,7,11,17-tetraazabicyclo[13.3.1 ]heptadeca-1(17),13,15-triene] (160 mg, 0.128 mmol) in conc. H$_2$SO$_4$ (2.5 ml) was stirred at 105° C. for 2 hours. The dark brown solution was cooled to room temperature and the pH adjusted to 14 with 10N NaOH. The aqueous phase was extracted with CHCl$_3$ (20 ml, x3), the combined organic phases were dried (MgSO$_4$) and concentrated in vacuo affording a pale yellow oil. To a stirred solution of the oil in 5 ml of anhydrous EtOH was passed HBr (g) resulting in a tan precipitate. After stirring for 15 minutes at room temperature the solid was collected by filtration. The tan solid was dissolved in 5 ml of H$_2$O, activated charcoal was added (100 mg) and the solution was heated for 30 minutes. The hot solution was eluted through celite and concentrated to approximately 2 ml. Glacial acetic acid was added-resulting in a white precipitate which was collected by filtration, washed with Et$_2$O and dried in vacuo giving 7,7'-[1,4-phenylenebis(methylene)]-bis[15-methoxy-3,7,11,17-tetraazabicyclo[13.3.1]heptadeca-1(17),13,15-triene] hexahydrobromide dihydrate (65 mg, 44%) as a white solid. $^1$H NMR (D$_2$O) δ 2.14–2.26 (m, 8H), 3.00–3.10 (m, 8H), 3.12–3.23 (m, 8H), 3.80 (s, 6H), 4.25 (s, 4H), 4.35 (s, 8H), 7.01 (s, 4H), 7.43 (s, 4H). $^{13}$C NMR (D$_2$O) δ 19.25, 42.98, 48.21, 49.12, 55.99, 58.26, 110.80, 130.46, 132.16, 151.63, 167.99. Mass spectrum (FAB); m/e (relative intensity); 713 (M+HBr, 41), 711 (M+HBr, 40), 631 (M+1, 100), 617 (14), 416 (12), 368 (13). IR (KBr): 1607 cm$^{-1}$ (C=C—OMe). C$_{36}$H$_{64}$N$_8$O$_4$Br$_6$ requires C, 37.52; H, 5.60; N, 9.72; Br, 41.60: Found: C, 37.64; H, 5.45; N, 9.69; Br, 41.02.

Synthesis of Compound D 7,7'-[1,4-Phenylenebis(methylene)]bis-3,7,11,17-tetraazabicyclo-[13.3.1]-heptadeca-13,16-triene-15-one octahydrobromide To a stirred solution of 7,7'-[1,4-phenylenebis(methylene)]bis[15-methoxy-3,11-(p-toluenesulphonyl)-3,7,11,17-tetraazabicyclo[13.3.1]heptadeca-1(17),13,15-triene] (150 mg, 0.12 mmol) in acetic acid (6 ml) was added 48% hydrobromic acid (4 ml) and the solution was stirred at 115° C. for 46 hours resulting in a white precipitate. The solution was cooled to room temperature and diluted with Et$_2$O, the resulting white solid was collected by filtration, washed with glacial acetic acid and Et$_2$O giving 7,7'-[1,4-phenylenebis-(methylene)]bis-3,7,11,17-tetraazabicyclo[13.3.1]heptadeca-13,16-triene-15-one octahydrobromide (95 mg, 64%) as a white solid. $^1$H NMR (D$_2$O) δ 2.16–2.29 (m, 8H), 3.06 (t, 8H,. J=7.6 Hz), 3.27 (t, 8H, J=7.6 Hz), 4.31 (s, 8H), 4.34 (s, 4H), 6.85 (s, 4H), 7.48 (s, 4H). $^{13}$C NMR (D$_2$O): δ 19.1, 42.94, 48.20, 49.03, 58.30, 112.19, 130.29, 132.24, 151.63, 165.71. Mass spectrum (FAB): m/e (relative intensity); 685 (M+HBr, 5), 683 (M+HBr, 5), 603 (M+1, 100), 460 (12), 329 (16). IR (KBr) 1629 cm$^{-1}$ (C=O). C$_{34}$H$_{58}$N$_8$O$_2$Br$_8$ requires C, 32.66; H, 4.68; N, 8.96; Br, 51.13; found: C, 32.67; H, 4.67; N, 8.90; Br, 51.08.

EXAMPLE 4 a) N-Diethoxyphosphoryldiethanolamine

To a solution of diethanolamine (5.0 g, 48 mmol) and triethylamine (8.0 ml) in dichloromethane (75 ml) was added dropwise with stirring under Argon, a solution of diethylchlorophosphate (8.2 g, 48 mmol) in dichloromethane (25 ml) over approximately 15 minutes and then allowed to stir at room temperature overnight. The mixture was washed with brine (50 ml) then dried (Na$_2$SO$_4$) and evaporated in vacuo to give the crude product as a viscous oil. The oil was dissolved in ether (100 ml) and the white solid which precipitated was filtered off (triethylamine hydrochloride). The ether solution was evaporated in vacuo giving N-diethoxyphosphoryldiethanolamine (6.2 g, 54%) as a colourless oil.

b) N-Diethoxyphosphorylbis(2-methanesulphonyl) diethanolamine

To a solution of N-diethoxyphosphoryldiethanolamine (3.0 g, 12 mmol) and triethylamine (5.2 ml) in dichloromethane (50 ml), cooled to 0°–5° C., was added dropwise with stirring a solution of methanesulphonyl chloride (3.0 g, 26 mmol) in dichloromethane (25 ml) over approximately 15 minutes. The mixture was stirred at room temperature overnight, washed with saturated aqueous ammonium chloride (50 ml) and brine (50 ml) then dried ($Na_2SO_4$) and evaporated in vacuo to give N-diethoxyphosphorylbis(2-methanesulphonyl)diethanolamine (4.0 g, 81%) as a light brown oil.

2,6-Bis(cyanomethyl)pyridine

A stirred solution of 2,6-bis(bromomethyl)pyridine hydrobromide (6.0 g, 17 mmol, sodium cyanide (5.1 g, 104 mmol) and cetyltrimethylammonium bromide (633 mg, 1.7 mmol) in benzene/water (50 ml/25 ml) was heated to reflux for 4 hours. The reaction mixture was allowed to cool to room temperature and the organic layer separated. The aqueous layer was extracted with benzene (50 ml) and dichloromethane (75 ml). The combined organic extracts were dried ($Na_2SO_4$) and evaporated in vacuo to give a brown solid which was purified by filtration through basic alumina using dichloromethane (500 ml) as eluent giving 2,6-bis(cyanomethyl)pyridine (2.4 g, 86%) as a white solid.

2,6-Bis(2-aminoethyl)pyridine

To a solution of 2,6-bis(cyanomethyl)pyridine (4.3 g, 27 mmol) in methanol (75 ml, saturated with ammonia) was added Raney nickel (10.0 g, excess) and the mixture hydrogenated at 45 psi and room temperature for 48 hours. The catalyst was filtered off and the solvent evaporated in vacuo to give 2,6-bis(2-aminoethyl)pyridine as a brown viscous oil (3.7 g, 83%). This was used without further purification.

2,6-Bis(N,N'-p-toluenesulphonyl-2-aminoethyl) pyridine

To a stirred solution of 2,6-bis(2-aminoethyl)pyridine (3.8 g, 23 mmol) and triethylamine (7.0 ml) in dichloromethane (75 ml) was added dropwise with stirring a solution of p-toluenesulphonyl chloride (8.7 g, 49 mmol) in dichloromethane (25 ml) over approximately 15 minutes and then allowed to stir at room temperature overnight. The mixture was washed with saturated aqueous sodium bicarbonate (50 ml) and brine (50 ml) then dried ($Na_2SO_4$) and evaporated in vacuo to give the crude product as a pale yellow viscous oil. The crude product was purified by column chromatography on silica gel using dichloromethane/methanol (98/2) as the eluent, whereby 2,6-bis(N,N'-p-toluenesulphonyl-2-aminoethyl)pyridine (8.0 g, 75%) was obtained as a white solid.

7-Diethoxyphosphoryl-4,10,bis(p-toluenesulphonyl)-4,7,10,17-tetraazacyclo[13.3.1]heptadeca-1(17),13,15-triene To a stirred solution of 2,6-bis(N,N'-p-toluenesulphonyl-2-aminoethyl)pyridine (5.7 g, 12 mmol) in DMF (550 ml) containing cesium carbonate (13.7 g, 42 mmol) maintained at 55° C. was added a solution of N-diethoxyphosphorylbis(2-methanesulphonyl)diethanolamine (4.8 g, 12 mmol) in DMF (55 ml) dropwise over a period of 16–18 hours. The reaction mixture was stirred at 55° C. for a total of 30 hours then allowed to cool to room temperature and evaporated in vacuo. The brown residue which was partitioned between dichloromethane (700 ml) and brine (350 ml). The organic layer was separated, dried ($Na_2SO_4$) and evaporated in vacuo to give the crude product as a light brown solid. Column chromatography on silica gel using ethyl acetate/ hexane (70/30) as eluent gave 7-diethoxyphoshory14,10-bis(p-toluenesulphonyl)-4,7,10,17-tetraazacyclo[13.3.1] heptadeca-1(17),13,15-triene (1.83 g, 23%) as a white solid.

4,10-Bis(p-toluenesuphonyl)-4,7,10,17-tetraazabicyclo[13.3.1]heptadeca-1(17),13,15-triene Using the general procedure in example 1 e 7-Diethoxyphosphoryl-4,10-bis(p-toluenesulphonyl)-4,7,10,17-tetraazacyclo[13.3.1]heptadeca-1(17),13,15-triene (1.5 g) gave 4,10-bis(p-toluene-sulphonyl)-4,7,10,17-tetraazabicyclo[13.3.1]heptadeca-1(17),13,15-triene (1.2 g, 92%) as a white solid.

7,7'-[1,4-Phenylenebis(methylene)]bis[4,10-bis(p-toluenesulphonyl)-4,7,10,17-tetraazabicyclo[13.3.1] heptadeca-1(17),13,15-triene]

Using the general produre in example 1f 4,10-Bis(p-toluenesulfonyl)-4,7,10,17-tetraazabicyclo [13.3.1]-heptadeca-1(17),13,15-triene (1.1 g, 2 mmol) and α,α'-dibromo-p-xylene (265 mg, 1 mmol) gave 7,7'-[1,4-phenylenebis(methylene)]bis[4,10-bis(p-toluenesulphonyl)-4,7,10,17-tetraazabicyclo[13.3.1]heptadeca-1(17), 13,15-triene] (900 mmg, 84%) as a white amorphous solid.

Synthesis of Compound E

7,7'-[1,4-Phenylenebis(methylene)]bis-4,7,10,17-tetraazabicyclo-[13.3.1]heptadeca-1(17),13,15-triene octahydrobromide tetrahydrate 7,7'-[1,4-Phenylenebis(methylene)]bis[4,10-bis(p-toluenesulphonyl)-4,7,10,17-tetraazabicyclo[13.3.1] heptadeca-1(17),13,15-triene] (120 mg) was dissolved in concentrated sulfuric acid (2.0 ml) and stirred rapidly at 100° C. for 3 hours. The resulting mixture was cooled and carefully made basic with sodium hydroxide solution (10 ml, 10N). The solution was extracted with dichlommethane (2×100 ml), dried ($Na_2SO_4$) and evaporated in vacuo giving the free base as a white solid. The solid was dissolved in acetic acid (5.0 ml) and HBr/acetic acid (30%, Aldrich) (0.5 ml) added and the reaction mixture stirred at room temperature for 5 minutes. Ether (50 ml) was added to precipitate the product. The white solid was allowed to settle to the bottom of the flask and the supernatant solution was decanted off. The solid was washed by decantation with ether three times and the remaining traces of ether removed by evaporation under reduced pressure giving 7,7'-[1,4-phenylenebis (methylene)]bis-4,7,10,17-tetraazabicyclo[13.3.1] heptadeca-1(17),13,15-triene octahydrobromide tetrahydrate (88 mg, 72%) as a white solid. $^1$H NMR ($D_2O$) δ 2.75 (m, 8H), 3.05–3.65 (m, 28H), 6.88,(s, 4H), 7.15 (d, 4H, J=7.5 Hz), 7.65 (t, 2H, J=7.5 Hz). Mass spectrum (FAB); m/e (relative intensity); 653 (M+HBr, 22), 651 (M+HBr, 22), 571 (M+1, 31), 339 (21), 235 (100). $C_{34}H_{66}N_8Br_8O_4$/ 0.5 acetic acid requires: C, 31.84; H, 5.19; N, 8.49; Br, 48.42; Found: C, 32.04; H, 5.14;N, 8.50; Br, 48.25.

EXAMPLE 5

N-Diethoxyphosphoryl-bis(3-methanesulphonyl) dipropanolamine was prepared from dipropanolamine (D. B. Denny et al *J Am Chem Soc*, 1980, 102, 5073–5077) using procedures a and b, Example 4.

8-Diethoxyphosphoryl-4,12-bis(p-toluenesulphonyl)-4,8,12,19-tetraazabicyclo[15.3.1]nonadeca-1(19), 15,17-triene General procedure To a stirred solution of 2,6-bis(N,N'-p-toluenesulphonyl-2-amino-ethyl)pyridine (2.2 g, 5 mmol) in DMF (200 ml) containing finely ground anhydrous cesium carbonate (5.2 g, 16 mmol) maintained at 55° C. under argon was added a solution of N-diethoxyphosphoryl-bis(3-methanesulphonyl) dipropanolamine (2.2 g, 5 mmol) in DMF (75 ml) dropwise over a period of 16–18 hours. The reaction mixture was stirred at 55° C. for a total of 30 hours then allowed to cool and evaporated in vacuo. The brown residue was partitioned in dichloromethane (250 ml) and brine (150 ml). The organic layer was separated and dried ($Na_2SO_4$) then evaporated in vacuo to give the crude product as a brown solid. Column chromatography on silica gel using dichloromethane/methanol (97/3) as the eluent gave 8-diethoxyphosphoryl-4,12-bis(p-toluenesulphonyl)-4,8,12,19-tetraazacyclo[15.3.1]nonadeca-1(19),15,17-triene (1.5 g, 48%) as a white solid.

4,12-Bis(p-toluenesulphonyl)-4,8,12,19-tetraazabicyclo[15.3.1]nonadeca-1(19),15,17-triene Using the general procedure in example 1e 8-Diethoxyphosphoryl-4,12-bis(p-toluenesulphonyl)-4,8,12,19-tetraazacyclo[15.3.1]nonadeca-1(19),15,17-triene (780 mg) gave 4,12-bis(p-toluene-sulphonyl)-4,8,12,19-tetraazabicyclo[15.3.1]nonadeca-1(19),15,17-triene (700 mg, 97%) as a white solid.

8,8'-[1,4-Phenylenebis(methylene)]bis[4,12-bis(p-toluenesulphonyl)-4,8,12,19-tetraazabicyclo[15.3.1]nonadeca-1(19),15,17-triene]

Using the general procedure in example 1f 4,12-Bis(p-toluenesulphonyl)-4,8,12,19-tetraazabicyclo[15.3.1]-nonadeca-1(19),15,17-triene (534 mg) and α,α'-dibromo-p-xylene (124 mg) gave 8,8'-[1,4-phenylenebis(methylene)]bis[4,12-bis (p-toluenesulphonyl)]-4,8,12,19-tetraazabicyclo[15.3.1]nonadeca-1(19),15,17-triene] (460 mg, 83%) as a white solid.

Synthesis of Compound F

8,8'-[1,4-Phenylenebis(methylene)]bis-4,8,12,19-tetraazabicyclo[15.3.1]nonadeca-1(19),15,17-triene octahydrobromide heptahydrate To a solution of 8,8'-[1,4-phenylenebis(methylene)]bis[4,12-bis(p-toluenesulphonyl)]-4,8,12,19-tetraazabicyclo[15.3.1]nonadeca-1(19),15,17-triene] (150 mg) in acetic acid (2.5 ml) was added hydrobromic acid (Aldrich, 48% aqueous, 1.5 ml) and the mixture heated to reflux with stirring for 18 hours. The mixture was cooled and ether (50 ml) added to precipitate the product. The white solid was allowed to settle to the bottom of the flask and the supernatant solution was decanted off. The solid was then washed by decantation with ether three times and the remaining traces of ether removed by evaporation under reduced pressure and drying in vacuo overnight giving 8,8'-[1,4-Phenylenebis(methylene)]bis-4,8,12,19-tetraazabicyclo[15.3.1]nonadeca-1(19),15,17-triene octahydrobromide heptahydrate as a white solid (100 mg, 65%). $^1$H NMR ($D_2O$) δ 2.13 (m, 8H), 3.06–3.39 (M, 32H), 4.41 (s, 4H), 7.13 (d, 4H, J=7.5 Hz), 7.51 (s, 4H), 7.65 (t, 2H, J=7.5 Hz). Mass spectrum (FAB); m/e (relative intensity); 709 (M+HBr, 33), 707 (M+HBr, 33), 627 (M+1, 83), 367 (100). $C_{38}H_{80}N_8Br_8O_7$ requires: C, 32.59; H, 5.76; N, 8.00; Br, 45.65; Found: C, 32.44; H, 5.28; N, 7.49; Br, 46.51.

EXAMPLE 6

N-Diethoxyphosphorylbis(2-azido)diethylamine

N-Diethoxyphosphorylbis(2-methanesulphonyl) diethanolamine (see Example 4b) (5.4 g, 14 mmol) was dissolved in DMF (25 ml) containing sodium azide (3.3 g, 35 mmol) and stirred at 80° C. under argon for 18 hours. The reaction mixture was cooled and concentrated in vacuo. The brown residue was partitioned between ethyl acetate (200 ml) and water (200 ml). The organic layer was separated, dried ($Na_2SO_4$) and evaporated under reduced pressure to give N-diethoxy-phosphorylbis(2-azido)diethylamine (2.7 g, 68%) as a colourless oil.

N-Diethoxyphosphoryi-2,2'-iminobisethylamine

To a solution of the above diazide (10.4 g, 36 mmol) in ethyl acetate (75 ml) was added palladium on carbon (10%, 5.0 g) and the mixture was hydrogenated at 45 psi and room temperature for 18 hours. The catalyst was filtered off and the solvent evaporated in vacuo to give N-diethoxyphosphoryl-2,2'-iminobisethylamine (6.4 g, 76%) as a colourless oil.

N-Diethoxyphosphoryi-N',N''-bis(p-toluenesulphonyl)-2,2'-iminobisethylamine

To a solution of N-diethoxyphosphoryl-2,2'-iminobisethylamine (4.7 g, 20 mmol) and triethylamine (5.8 ml) in dichloromethane (100 ml) was added dropwise with stirring a solution of p-toluene sulphonyl chloride (7.9 g, 40 mmol) in dichloromethane (25 ml) over approximately 15 minutes and then allowed to stir at room temperature overnight. The mixture was washed with saturated aqueous sodium bicarbonate (50 ml) and brine (50 ml), then dried ($Na_2SO_4$) and evaporated in vacuo to give N-diethoxyphosphoryl-N',N''-bis(p-toluenesulphonyl)-2,2'-imino bisethylamine (10.2 g, 95%) as a colourless oil.

6-Diethoxyphosphoryl-3,9-bis(p-toluenesulphonyl)-3,6,9,15-tetraazabicyclo[11.3.1]pentadeca-1(15),11,13-triene Using the general procedure in example 1d N-Diethoxyphosphoryl-N',N''-bis(p-toluenesulphonyl)-2,2'-iminobis-ethylamine (2.4 g, 4.4 mmol) and 2,6-bis-(dibromomethyl)pyridine hydrobromide (1.5 g, 4.5 mmol) gave 6-diethoxyphosphoryl-3,9-bis(p-toluenesulphonyl)-3,6,9,15-tetraazabicyclo[11.3.1]pentadeca-1(15),11,13-triene (2.0 g, 68%) as a white solid.

3,9-Bis(p-toluenesulphonyl)-3,6,9,15-tetraazabicyclo[11.3.1]pentadeca-1(15),11,13-triene Using the general procedure in example 1e 6-Diethoxyphosphoryl-3,9-bis(p-toluenesulphonyl)-3,6,9,15-tetraazabicyclo[11.3.1]pentadeca-1(15),11,13-triene (650 mg) gave 3,9-bis(p-toluene-sulphonyl)-3,6,9,15- tetraazabicyclo[11.3.1]pentadeca-1(15),11,13-triene (41-1 mg, 80%) as a white solid.

6,6'-[1,4'-Phenylenebis(methylene)]bis [3,9-bis(p-toluenesulphonyl)-3,6,9,15-tetraazabicyclo[11.3.1]pentadeca-1(15),11,13-triene]

Using the general procedure in Example 1f 3,9-B is(p-toluenesulphonyl)-3,6,9,15-tetraazabicyclo[11.3.1]pentadeca-1(15),11,13-triene (540 mg, 1.1 mmol) and α,α'-dibromo-p-xylene (140 mg, 0.53 mmol) gave 6,6'-[1,4'-phenylenebis (methylene)]bis[3,9-bis(p-toluenesulphonyl)-3,6,9,15-tetraazabicyclo[11.3.1]pentadeca-1(15),11,13-triene] (400 mg, 67%) as a white solid.

Synthesis of Compound G

6,6'-[1,4'-Phenylenebis(methylene)]bis-3,6,9,15-tetraazabicyclo[11.3.1]pentadeca-1(15),11,13-triene hexahydromide trihydrate 6,6'-[1,4'-Phenylenebis(methylene)]bis[3,9-bis(p-toluenesulphonyl)-3,6,9,15-tetraazabicyclo[11.3.1]pentadeca-1(15), 11,13-triene] (90 mg) was dissolved in concentrated sulfuric acid (2.0 ml) and stirred rapidly at 100° C. for 3 hours. The resulting mixture was cooled and carefully basified with sodium hydroxide solution (10 ml, 10N). The solution was extracted with dichloromethane (2×100 ml), dried ($Na_2SO_4$) and evaporated in vacuo giving the free base as a white solid. The solid was dissolved in acetic acid (5.0 ml) and HBr/acetic acid (30%, Aldrich) (0.5 ml) added and the reaction mixture stirred at room temperature for 5 minutes. Ether (50 ml) was added to precipitate the product. The white solid was allowed to settle to the bottom of the flask and the supernatant solution was decanted off. The solid was washed by decantation with ether three times and the remaining traces of ether removed by evaporation under reduced pressure and drying in vacuo overnight, giving 6,6'-[1,4'-phenylenebis(methylene)]bis-3,6,9,15-tetraazabicyclo[11.3.1]-pentadeca-1(15),11,13-triene hexahydromide trihydrate (25 mg, 33%) as a white solid. $^1$H NMR ($D_2O$) δ 2.65 (m, 8H), 3.05 (m, 8H), 3.75 (s, 4H), 4.45 (s, 8H), 7.20 (d, 4H, J=7.5 Hz), 7.26 (s, 4H), 7.85 (t, 2H, J=7.5 Hz). Mass spectrum (FAB); m/e (relative intensity); 595 (M+HBr, 9), 593 (M+HBr, 9), 515 (M+1, 57), 440 (48), 223 (100). $C_{30}H_{54}N_8Br_6O_3$ requires: C, 34.18; H, 5.16; N, 10.62; Br, 45.48; Found: C, 34.25; H, 5.17; N, 10.56; Br, 43.60.

EXAMPLE 7

6,6'-[1,3-Phenylenebis(methylene)]bis[3,9-bis(p-toluenesulphonyl)-3,6,9,15-tetraazabicyclo[11.3.1]pentadeca-1(15),11,13-triene]

Using the general procedure in example 1f 3,9-Bis(p-toluenesulphonyl)-3.6.9.15-tetraaza[11.3.1]pentadeca-1(15),11,13-triene (514 mg, 1 mmol) and α,α'-dibromo-m-xylene (132 mg, 0.55 mmol) gave 6,6'-[1,3-phenylenebis (methylene)]bis[3,9-bis(p-toluenesulphonyl)-3.6.9.15-tetraazabicyclo[11.3.1]pentadeca-1(15),11,13-triene] (531 mg, 94%) as a white solid.

Synthesis of Compound H

6,6'-[1,3-Phenylenebis(methylene)]bis-3,6,9,15-tetraazabicyclo[11.3.1]pentadeca-1(15),11,13-triene hexahydrobromide trihydrate 6,6'-[1,3-Phenylene-bis(methylene)]bis[3,9-bis(p-toluenesulphonyl)-3,6,9,15-tetraazabicyclo[11.3.1]pentadeca-1(15),11,13-triene] (100 mg) was de-protected with concentrated sulphuric acid using the procedure described in Example 6 (synthesis of G) giving 1,1'-[1,3-phenylenebis(methylene)]bis-3,6,9,15-tetraazabicyclo [11.3.1]pentadeca-1(15),11,13-triene hexahydrobromide trihydrate (42 mg, 45%) as a white solid. $^1$H NMR ($D_2O$) δ 2.66 (m, 8H), 3.11 (m, 8H), 3.76 (s, 4H), 4.45 (s, 8H), 7.26–7.29 (m, 8H), 7.78 (t, 2H, J=7.5 Hz). Mass spectrum (FAB); m/e (relative intensity); 595 (M+HBr, 9), 593 (M+HBr, 9), 515 (M+1, 100); $C_{30}H_{54}N_8Br_6O_3$ requires: C, 34.18; H, 5.16; N, 10.63; found: C, 34.43; H, 5.28; N, 10.15.

EXAMPLE 8

8-Diethoxyphosphoryl-4,12-bis(p-toluenesulphonyl)-1-oxa-4,8,12-triazatetradecane To a stirred solution of N-diethoxyphosphoryl-N',N''-bis(p-toluene-sulphonyl)-3,3'-iminobispropylamine (2.9 g, 5 mmol) in DMF (150 ml) containing cesium carbonate (4.1 g, 13 mmol, 2.5 equiv.) maintained at 55° C. under argon was added a solution of 2-bromoethyl ether (Aldrich, 1.16 g, 5 mmol) in DMF (75 ml) dropwise over a period of 16–20 hours. The reaction mixture was stirred at 55° C. for a total of 30 hours then allowed to cool to room temperature and evaporated to dryness under reduced pressure. The brown residue was partitioned in dichloromethane (150 ml) and brine (150 ml). The organic layer was separated then dried ($Na_2SO_4$) and evaporated in vacuo to give the crude product as a yellow oil. Column chromatography using dichloromethane/methanol (97/3) as the eluent, gave 8-diethoxyphosphoryl-4,12-bis(p-toluenesulphonyl)-1-oxa-4,8,12-triazatetra-decane (1.1 g, 79%) as a colourless oil.

4,12-Bis(p-toluenesulphonyl)-1-oxa-4,8,12-triazatetradecane

Using the general procedure in example 1e

8-Diethoxyphosphoryl-4,12-bis(p-toluenesulphonyl)-1-oxa-4,8,12-triazatetradecane (750 mg) gave 4,12-bis(p-toluenesulphonyl)-1-oxa-4,8,12-triazatetradecane (410 mg, 69%) as a white solid.

8,8'-[1,4-Phenylenebis(methylene)]bis[4,12-bis-(p-toluenesulphonyl)-1-oxa-4,8,12-triazatetradecane]

Using the general produre in example 1f 4,12-Bis(p-toluenesulphonyl)-1-oxa-4,8,12-triazatetradecane (403 mg, 0.79 mmol) and α,α'-dibromo-p-xylene (105 mg, 0.40 mmol) gave 8,8'-[1,4-phenylenebis (methylene)]bis[4,12-bis-(p-toluenesulphonyl)-1-oxa-4,8,12-triazatetradecane] (393 mg, 89%) as a white solid.

Synthesis of Compound J

8,8'-[1,4-Phenylenebis(methylene)]bis-1-oxa-4,8,12-triazatetradecane-hexahydro bromide trihydrate To a solution of 8,8'-[1,4-phenylenebis(methylene)]bis[4,12-bis-(p-toluenesulphonyl)-1-oxa4,8,12-triazatetradecane] (250 mg) in acetic acid (2.5 ml) was added hydrobromic acid (Aldrich, 48% aqueous, 1.5 ml) and the mixture was heated to reflux with stirring for 18 hours. The mixture was allowed to cool and ether (50 ml) was added to precipitate the product. The white solid was allowed to settle to the bottom of the flask and the supernatant solution was decanted off. The solid was then washed by decantation with ether three times and the remaining traces of ether removed by evaporation under reduced pressure and drying in vacuo overnight giving 8,8'-[1,4-phenylenebis(methylene)]bis-1-oxa-4,8,12-triazatetra-decanehexahydrobromide trihydrate as a white solid (221 mg, 62%). $^1$H NMR (D$_2$O) δ 2.05 (m, 8H), 3.15–3.35 (m, 24H), 3.75 (m, 8H), 4.25 (s, 4H), 7.55 (s, 4H). Mass spectrum (FAB); m/e (relative intensity); 587 (M+HBr, 49), 585 (M+HBr, 49), 506 (M+1, 100), 307 (41). C$_{28}$H$_{64}$N$_6$Br$_6$O$_5$ requires: C, 32.20; H, 6.18; N, 8.05; Br, 45.91. Found: C, 31.73; H, 5.86; N, 7.42; Br, 46.59.

EXAMPLE 9

3,6,14-Tris(p-toluenesulphonyl)-3,6,14,17,23,24-hexaazatricyclo-[17.3.1.1$^{8,12}$]tetracosa-1(23),8,10,12(24),19,21;hexaene To a stirred solution of 3,6,14,17,23,24-hexaazatricyclo-[17.3.1.1$^{8,12}$]tetracosa-1(23),8,10,12(24),19,21-hexaene (460 mg, 1.41 mmol) (G L Rothermel, L Miao, A L Hill, L C Jackels, *Inorg Chem*, 1992, 31, 4854) and triethylamine (0.60 ml, 4.233 mmol) at 0° C. in 40 ml of CH$_2$Cl$_2$ under an argon atmosphere was added a solution of p-toluenesulphonyl chloride (804 mg, 4.233 mmol) in 10 ml of CH$_2$Cl$_2$ dropwise over 15 min. The solution was stirred at 0° C. for 30 minutes and warmed to room temperature and stirred a further 4 hours. The reaction mixture was quenched with saturated NH$_4$Cl (10 ml), the aqueous phase extracted with CH$_2$Cl$_2$, dried over MgSO$_4$ and concentrated in vacuo. The residue was purified by column chromatography on silica gel using 5% MeOH in CH$_2$Cl$_2$ as eluent giving 3,6,14-tris(p-toluenesulphonyl)-3,6,14,17,23,24-hexaazatricyclo[17.3.1.1$^{8,12}$]tetracosa-1(23),8,10,12(24),19,21-hexaene (300 mg, 27%) as a white solid.

17,17'-[1,4-Phenylenebis(methylene)]bis[3,6,14-tris(p-toluenesulphonyl)-3,6,14,17,23,24-hexaazatricyclo[17.3.1$^{8,12}$]tetracosa-1(23),8;10,12(24),19,21-hexaene]

Using the general procedure in Example 1f 3,6,14-Tris(p-toluenesulphonyl)-3,6,14,17,23,24-hexaazatricyclo-[17.3.1.1.$^{8,12}$]tetracosa-1(23),8,10,12(24), 19,21-hexaene (300 mg, 0.381 mmol) and α,α'-dibromo-p-xylene (50 mg, 0.19 mmol) gave 17,17'-[1,4-phenylenebis-(methylene)]bis[3,6,14-tris(p-toluenesulphonyl)-3,6,14,17, 23,24-hexaazatricyclo-[17.3.1.1$^{8,12}$]tetracosa-1(23),8,10,12 (24),19,21-hexaene] (280 mg, 88%) as a fluffy white solid.

Synthesis of Compound K 17,17'-[1,4-Phenylene-bis(methylene)]bis-3,6,14,17,23,24-hexaazatricyclo[17.3.1.1$^{8,12}$] tetracosa-1(23),8,10,12(24),19,21-hexnene octahydrobromide A solution of 17,17'-[1,4-phenylenebis(methylene)]bis[3, 6,14-tris(p-toluenesulphonyl)-3,6,14,17,23,24-hexaazatricyclo[17.3.1.1$^{8,12}$]tetracosa-1(23),8,10,12(24), 19,21-hexaene] (280 mg, 0.166 mmol) in conc H$_2$SO$_4$ (2 ml) was stirred at 110° C. for 2 hours. The dark brown solution was cooled to room temperature and the pH adjusted to 14 with the addition of 10N NaOH. The aqueous phase was extracted with CHCl$_3$ (20 ml, x 3), the combined organic phases were dried over MgSO$_4$ and concentrated in vacuo thus affording a pale yellow oil. To a stirred solution of the oil in 10 ml of anhydrous EtOH was passed HBr(g) resulting in a white solid precipitate. After stirring for 15 minutes at room temperature the solid was filtered off, washed with ether and dried in vacuo giving 17,17'-[1,4-phenylenebis (methylene)]bis-3,6,14,17,23,24-hexaazatricyclo-[17.3.1.1$^{8,12}$]tetracosa-1(23),8,10,12(24),19,21-hexaene octahydrobromide (135 mg, 58%) as a white solid. $^1$H NMR (D$_2$O) δ 3.73 (s, 8H), 3.94 (s, 8H), 4.38 (s, 8H), 4.45 (s, 8H), 6.86 (d, 2H, J=8.6 Hz), 7.19–7.24 (m, 6H), 7.47 (d, 4H, J=8.6 Hz), 7.56 (t, 2H, J=8.6 Hz), 7.87 (t, 2H, J=8.6 Hz). $^{13}$C NMR (D$_2$O) δ 44.86, 46.77, 47.03, 53.41, 53.66, 56.18, 60.24, 124.83, 125.00, 125.06, 125.85, 132.32, 134.83, 141.99, 142.06, 152.20, 152.31, 152.41. Mass spectrum (FAB); m/e (relative intensity); 838 (M+HBr, 4), 836 (M+HBr, 4), 756 (M+1, 14), 429 (20), 307 (60), 215 (100). C$_{44}$H$_{66}$N$_{12}$Br$_8$ requires C, 37.68; H, 4.74; N, 11.98; Br, 45.58; Found: C, 37.86; H, 4.94; N, 11.90; Br, 45.33.

The general reaction schemes are illustrated in the attached sheets 1 to 6.

The compounds of the invention were tested in a screen by the MTF method (*J Virol Methods* 120:309–321[1988]). MT-4 cells (2.5×10$^4$/well) were challenged with HIV-1 (HTLV-IIIB) or HIV-2 (LAV-2 ROD) at a concentration of 100 CCID$_{50}$ and incubated in the presence of various concentrations of the test compounds, which were added immediately after challenge with the virus. After 5 days culture at 37° C. in a CO$_2$ incubator, the number of viable cells was assessed by the MTT (tetrazolium) method. Antiviral activity and cytotoxicity of the compounds are expressed in the Table below as IC$_{50}$ (μg/ml) and CC$_{50}$ (μg/ml), respectively. The potential therapeutic usefulness was assessed by calculating a Selectivity Index (SI) corresponding to the ratio of CC$_{50}$ to IC$_{50}$. The results for the compounds of the invention are shown below in Table 1.

Compound L is 1,1'-[1,4-phenylenebis(methylene)]bis-1,4,8,11-tetraazacyclotetra-decane octahydrobromide dihydrate, (see WO 93/12096).

TABLE 1

| | HIV-1 (III$_B$) | | | HW-2 (ROD) | | |
|---|---|---|---|---|---|---|
| CMPD | IC$_{50}$ μg/ml | CC$_{50}$ μg/ml | SI | IC$_{50}$ μg/ml | CC$_{50}$ μg.ml | SI |
| A | 0.719 | >250 | 348 | 3.51 | >250 | 71 |
| B | 0.89 | 12.52 | 14 | — | — | — |
| C | 3.57 | 229 | 64 | 9.74 | >250 | 26 |
| D | >218 | >218 | <1 | >250 | >250 | <1 |
| E | 0.0014 | >250 | 1.76 × 10$^5$ | 0.001 | >250 | 2.47 × 10$^5$ |
| F | 0.59 | 199 | 336 | 1.68 | 171 | 102 |
| G | 0.62 | 6.0 | 10 | 0.15 | 4.71 | 31 |
| H | 0.104 | 32.11 | 309 | 0.0027 | 30.70 | 1.12 × 10$^4$ |
| J | 4.62 | >250 | >54 | 2.15 | >250 | >116 |
| K | 4.59 | 4.59 | <1 | 5.89 | 5.89 | <1 |
| L | 0.0068 | >250 | 3.37 × 10$^4$ | 0.009 | >250 | 2.79 × 10$^4$ |

The compounds were additionally studied to determine their partition coefficients as between octanol and water, in standard tests at various pH values. A partition coefficient greater than unity at pH 7–9 is generally considered to be a good indication that the compound will be absorbed through the upper gastrointestinal tract when dosed orally. Certain of the compounds of the invention demonstrate very significant activity against HIV combined with good partition coefficients, and thus are indicated for oral administration.

| | OCTANOL/BUFFER PARTITION COEFFICIENTS | | |
|---|---|---|---|
| COMPOUND | pH 7 | pH 8 | pH 9 |
| A | | 0.109 | 5.17 |
| B | 0.1 | 3.87 | 29.14 |

-continued

| COMPOUND | OCTANOL/BUFFER PARTITION COEFFICIENTS | | |
|---|---|---|---|
| | pH 7 | pH 8 | pH 9 |
| C | | 0.11 | 0.87 |
| D | | 0.025 | 0.23 |
| E | 0.004 | 0.036 | 3.012 |
| J | 0.003 | 0.012 | 0.739 |
| K | | 0.07 | 1.78 |
| L | 0.0016 | 0.005 | 0.16 |

The compounds of Formula I may be administered in free base form or in pharmaceutically acceptable acid addition salt or metal complex form. Such salts and complexes may be prepared in conventional manner as described in the Examples, and exhibit the same order of activity as the free bases. Pharmaceutical compositions containing compounds of Formula I may be manufactured in conventional manner containing active ingredient in association with a pharmaceutically acceptable carrier or diluent. Unit dosages forms contain for example from about 0.5 mg to about 100 mg of a compound of Formula I in free base or pharmaceutically acceptable acid addition salt form. Pharmaceutical compositions for oral administration are well known and may be formulated in accordance with generally known principles. Such compositions may be in solid form as tablets, capsules or dragees or in liquid form as a syrup or suspension.

We claim:

1. Linked polyamine cyclic compounds of general formula I,

V—R—A—R'—W    (I)

in which V and W are independently cyclic polyamine moieties having from 9 to 32 ring members and from 3 to 8 amine nitrogens in the ring spaced by 2 or more carbon atoms from each other, and having one or more aromatic or heteroaromatic rings fused thereto, A is an aromatic or heteroaromatic moiety when V and W have one or more aromatic or heteroaromatic moieties fused thereto, with or without an additional heteroatom other than nitrogen incorporated in the ring, or A is an aromatic or heteroaromatic moiety when V and W contain a heteroatom other than nitrogen incorporated in the ring without having one or more aromatic or heteroaromatic moieties fused thereto, and R and R' are each a substituted or unsubstituted alkylene chain or heteroatom-containing chain which spaces the cyclic polyamines and the moiety A, and their acid addition salts and metal complexes.

2. Compounds according to claim 1, wherein R and R' are each methylene.

3. Compounds according to claim 1 or 2, wherein moiety A is 1,3- or 1,4-phenylene.

4. Compounds according to any one of the preceding claims, wherein each V and W is an unsubstituted or substituted tricyclic or bicyclic ring system containing only carbon and nitrogen atoms in the rings.

5. Compounds according to claim 4, wherein one of the cyclic ring systems is a 10 to 20 membered polyamine ring system having from 3 to 6 amine nitrogen atoms and the ring system or systems is a fused benzyl or pyridinyl ring system.

6. The compound of claim 1 which is 7,7'-[1,4-phenylene-bis(methylene)]bis-3,7,11,17- tetraazabicyclo[13.3.1] heptadeca-1(17),13,15-triene.

7. The compound of claim 1 which is 7,7'-[1,4-phenylene-bis(methylene)]bis[15-chloro-3,7,11,17-tetraazabicyclo [13.3.1]heptadeca-1(17),13,15-triene].

8. The compound of claim 1 which is 7,7'-[1,4-phenylene-bis(methylene)]bis[15-methoxy-3,7,11,17-tetraazabicyclo [13.3.1]heptadeca-1(17),13,15-triene].

9. The compound of claim 1 which is 7,7'-[1,4-phenylene-bis(methylene)]bis-3,7,11,17-tetraazabicyclo[13.3.1]-heptadeca-13,16-triene-15-one.

10. The compound of claim 1 which is 7,7'-[1,4-phenylene-bis(methylene)]bis-4,7,10,17-tetraazabicyclo [13.3.1]-heptadeca-1(17),13,15-triene.

11. The compound of claim 1 which is 8,8'-[1,4-phenylene-bis(methylene)]bis-4,8,12,19-tetraazabicyclo [15.3.1]nonadeca-1(19),15,17-triene.

12. The compound of claim 1 which is 6,6'-[1,4-phenylene-bis(methylene)]bis-3,6,9,15-tetraazabicyclo [11.3.1]pentadeca-1(15),11,13-triene.

13. The compound of claim 1 which is 6,6'-[1,3-phenylene-bis(methylene)]bis-3,6,9,15-tetraazabicyclo [11.3.1]pentadeca-1(15),11,13-triene.

14. The compound of claim 1 which is 17,17'-[1,4-phenylene-bis(methylene)]bis-3,6,14,17,23,24-hexaazatricyclo[17.3.1.1$^{8,12}$]tetracosa-1(23),8,10,12(24),19,21-hexaene.

15. A method for the production of compounds according to claim 1, which method comprises nucleophilic attack by cyclic polyamines V' and W' each having a single unprotected ring amine nitrogen, all other amine nitrogens being protected, on a compound of formula III

X—R—A—R'—X    (III)

wherein R, R' and A are as defined above, and each X is an active substituent which can be displaced by the unprotected nitrogens of polyamines V' and W' and is preferably selected from Br, Cl, I, methanesulphonate, 4-tolylsulphonate and trifluoromethane sulphonate, and subsequently de-protecting the ring amine nitrogens.

16. A pharmaceutical composition active against HIV, comprising as an active ingredient a compound according to claim 1, in association or admixture with a pharmaceutically acceptable diluent or carrier.

17. A composition according to claim 16 in unit dosage form.

* * * * *